(12) United States Patent
Schecter

(10) Patent No.: US 8,214,039 B1
(45) Date of Patent: Jul. 3, 2012

(54) INDIVIDUALLY ADAPTED CARDIAC ELECTRO-MECHANICAL SYNCHRONIZATION THERAPY

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 1109 days.

(21) Appl. No.: 11/539,837

(22) Filed: Oct. 9, 2006

(51) Int. Cl.
*A61N 1/00* (2006.01)
(52) U.S. Cl. .......................................... 607/17; 607/119
(58) Field of Classification Search ............... 607/17, 607/119
See application file for complete search history.

(56) References Cited

U.S. PATENT DOCUMENTS

| | | | |
|---|---|---|---|
| 6,212,428 B1 * | 4/2001 | Hsu et al. ...................... | 600/515 |
| 6,292,693 B1 | 9/2001 | Darvish et al. | |
| 6,363,279 B1 | 3/2002 | Ben-Haim et al. | |
| 6,587,721 B1 | 7/2003 | Prutchi et al. | |
| 6,751,492 B2 * | 6/2004 | Ben-Haim ...................... | 600/374 |
| 7,505,810 B2 * | 3/2009 | Harlev et al. .................. | 600/509 |
| 2004/0220636 A1 | 11/2004 | Burnes | |
| 2005/0038481 A1 | 2/2005 | Chinchoy et al. | |
| 2005/0043895 A1 | 2/2005 | Schechter | |
| 2005/0182447 A1 | 8/2005 | Schecter | |

FOREIGN PATENT DOCUMENTS

| | | |
|---|---|---|
| WO | 0176691 A1 | 10/2001 |
| WO | 03092804 A1 | 11/2003 |
| WO | 2005018570 A2 | 3/2005 |
| WO | 2005018570 A3 | 3/2005 |
| WO | 2005018740 A1 | 3/2005 |
| WO | 2005020025 A2 | 3/2005 |
| WO | 2005020025 A3 | 3/2005 |

* cited by examiner

*Primary Examiner* — Nicole F Lavert

(57) ABSTRACT

A method of determining pacing therapy for an individual patient including determining representative electromechanical physiologic characteristics for a plurality of normal patients having a range of anatomical dimensions and developing a plurality of normal templates. Each template indicates the representative electromechanical physiologic characteristics of a group of normal patients having similar anatomical dimensions. The method can include measuring the anatomical dimensions of a dysfunctional patient, matching the dysfunctional patient with a template for normal patients having similar anatomical dimensions as the dysfunctional patient, determining the physiologic characteristics for the dysfunctional patient, determining indicated correction factors corresponding to any differences between the dysfunctional patient's physiologic characteristics and those of the matched template, and adjusting therapy delivery by any indicated correction factors to stimulate the patient in a pattern more closely matched to the physiologic characteristics of the matched template.

1 Claim, 7 Drawing Sheets

INDIVIDUALLY ADAPTED CARDIAC ELECTRO-MECHANICAL SYNCHRONIZATION THERAPY

FIELD OF THE INVENTION

The invention relates to the field of implantable cardiac stimulation devices and more particularly to improved devices and methods of providing therapy by improving multi-dimensional electro-mechanical synchronization of the patient's cardiac activity.

BACKGROUND OF THE INVENTION

Numerous people suffer from physical ailments affecting their heart function. Patients having diseased myocardium often exhibit one or more of impairment of the normal physiologic conduction system, myocardial stunning, hibernation, and/or myocardial necrosis. Of these symptoms, myocardial stunning, hibernation, and necrosis generally lead to hypocontractility of the cardiac muscle. Many patients also exhibit reduced cardiac output as a secondary symptom of a lack of myocardial contractility, impaired conduction, and/or deficiencies in the synchronicity of cardiac depolarization/repolarization. These factors generally result in impaired systolic and/or diastolic function which results in the commonly named congestive heart failure (CHF) or simply heart failure (HF).

Accordingly, a variety of therapies, including therapies automatically provided by therapeutic devices, have been developed and continue to be further developed for treatment of patients, including patients suffering from HF. One particular category of therapy which has been developed are referred to as cardiac stimulation devices. Such cardiac stimulation devices are frequently configured to be implanted in order to provide long term automatic monitoring of the patient's condition and to generate and deliver therapeutic cardiac stimulation as indicated. Implantable cardiac stimulation devices have been developed to monitor and provide therapy independently to multiple chambers of the patient's heart.

One particular category of implantable cardiac stimulation devices include the ability to monitor activity in and selectively deliver therapy to both of the patient's ventricles. This is frequently referred to as bi-ventricular or bi-V therapy. Implantable cardiac stimulation devices configured for bi-ventricular stimulation can be further configured to provide cardiac resynchronization therapy (CRT). CRT refers to modes of therapy which strive to restore a more closely normal synchronization between the patient's right and left ventricles. While CRT is as yet not effective with all patients suffering from HF, for many HF patients, CRT can improve the overall pumping effectiveness of an HF patient and thereby improve their quality of life. In at least certain patients, CRT can at least partially compensate for conduction/stimulation deficiencies to thereby improve synchronization of the electrical stimulation of the myocardium and/or to at least partially compensate for myocardial tissue having impaired contractility.

SUMMARY

While CRT has been shown to provide valuable benefits to certain HF patients, there remains a sizeable portion of the HF population that has been non-responsive or at best less responsive to existing CRT systems and algorithms. Percentages of patients develop worsening HF and might be improved if the implanted device were to be appropriately programmed for the individual patient, rather than at the pre-programmed, default values. Thus, it will be appreciated that there exists needs for improved systems and methods of delivering cardiac therapy both to improve the efficacy for patients who have exhibited positive response, as well as to provide new types of therapy for those patients who have exhibited less beneficial response. It would be beneficial to provide improved systems and methods of providing therapy which would be generally compatible with existing hardware platforms. It would be further advantageous to provide innovative systems and methods of providing therapy which would be compatible with improved hardware platforms.

Aspects of the invention include an innovative perspective on the combination of the patient's intrinsic activity and evoked activity responsive to therapeutic stimulation. Aspects of the invention are based at least in part on an approach that lack of responsiveness of certain patients to existing CRT systems is due at least partially to a mismatch between provided stimulation patterns and the patient's pathological deficiencies. Aspects of the invention strive to provide improved spatial and temporal synchronization between an individual patient's intrinsic electro-mechanical cardiac activity and any therapeutic stimulation provided in a multi-dimensional spatial and temporal perspective.

Aspects of the invention consider the patient's intrinsic physiology along multi-dimensional spatial vectors over time, and adjust the delivery of therapeutic stimulations to more closely equal a patient with matching anatomy and/or physiologic properties and appropriately delivered therapeutic stimulation. Such a patient is defined herein to have a eucontractile heart and an overall eucontractile function secondary to reverse remodeling and rectification of a prior pathophysiologic state. Additionally, a eucontractile cohort of patients can consist of those implanted with stimulation devices that provide for defibrillation but have structurally normal hearts (i.e. primary electrical abnormalities such Brugada syndrome, long QT syndrome).

As used herein, the terms "optimal", "optimize," "optimizing," "optimization", "minimize", "maximize" and the like are to be understood as commonly used terms of the art referring simply to a process of evaluating and adjusting or individualizing the operating parameters of a system for improved performance in an individual application. It will be understood that the physiologic activity and characteristics of an individual, for example their cardiac activity, is subject to both cyclical variations, diurnal variations, and long term variations. An individual patient's physiologic activity is also subject to variation brought about by medication dosing and environmental factors which are generally asynchronous and unpredictable by an automated therapy system. Thus, the matching of therapy systems and methods to precise instantaneous needs of a patient is as a practical matter an inexact science. Thus, use of the terms "optimal", "optimize," "optimizing," "optimization" and the like does not imply that the described process results in a perfect setting for the system or method as used with an individual patient or that any further improvements are not available. Thus, the terms "optimize," "optimizing," and/or "optimization" are to be interpreted as relative terms indicating generally improved performance in an individual application and are not to be interpreted as absolutes.

As used herein, eucontractile or eufunctional refers to physiologic activity that, at least in aspects of interest, is similar to that of a comparable healthy person. Eucontractile or eufunctional does not necessarily imply characteristics of a fully healthy normal person, but only characteristics that are similar to those that a normal healthy person would display. For example, a person can display eufunctional characteristics in certain physiological aspects and impaired characteristics in other physiological aspects.

Additional embodiments of the invention strive to optimize the performance of a therapy system to bring a patient into closer performance with a comparable "normal" or eucontractile patient. Patients who have not had a history of ischemic heart disease or cardiomyopathy, for example, patients with Brugada or Long QT syndromes, may nevertheless be implanted with cardiac stimulation systems. Such patients can be utilized to develop normalized templates indicating characteristic electro-mechanical activity of patients without diseased myocardium.

For example, in certain implementations, time impedance curves and intracardiac electrograms (IEGMs) can be taken over multiple different spatial vectors to determine characteristic normal or eucontractile characteristics for each of these vectors. The eucontractile patients can be further evaluated to determine their anatomical cardiac dimensions. The determined templates can thus be separated or grouped and averaged to develop a representative template for patients having similar anatomical dimensions.

A patient with diseased myocardium can then be evaluated for their individual cardiac anatomical dimensions. Once this is determined, they can then be matched with a template developed from other eucontractile patients having similar anatomical dimensions. The electro-mechanical characteristics of the diseased myocardial patient can then be compared with similar electro-mechanical characteristics from the template based on eucontractile patients and any differences determined. Any noted differences can be used to calculate correction factors to adjust a base therapy algorithm for the individual diseased myocardial patient in an attempt to drive their cardiac response more closely to that of the eucontractile template group. Depending on the indications of a particular application, certain embodiments can provide "forced fusion" wherein one or more chambers or regions of the patient's heart may experience both partial intrinsic and later partial paced or evoked response. These embodiments can, for example, provide improved therapy for a patient that has only a relatively small localized conduction impairment.

Yet additional embodiments of the invention provide therapy to restore a more closely normal spatial temporal depolarization/repolarization process. Normal cardiac contractility occurs in a generally helical or spiral fashion originating near the inflow of the right side chambers. The contractile pattern terminates in the left ventricular outflow tract beginning again in the subsequent cycle near the inflow of the right side chambers. Myofibril orientation generally follows this 3-dimensional helical pattern. Diastolic uncoiling and systolic coiling of the heart results in a progressive suction effect for diastolic inflow and a twisting, ringing effect for systolic output. This progressive helical process improves the hydrodynamic filling of cardiac chambers in diastole and systolic forward flow for cardiac output. Pathologic myocardium and/or conduction deficiencies alter and disrupt this progressive helical pattern and lead to diastolic and/or systolic dysfunction. Embodiments of the invention adapt the delivery of therapy in three spatial dimensions and temporally to attempt to restore closer conformance of the patient's contractility to the normal helical pattern.

One embodiment includes a method of determining therapy for an individual patient, the method including determining representative normal physiologic characteristics for a plurality of patients having a range of anatomical dimensions, developing a plurality of normal templates wherein each template indicates the representative normal physiologic characteristics of a group of patients having similar anatomical dimensions, measuring the anatomical dimensions of a dysfunctional patient, matching the dysfunctional patient with a template for patients having similar anatomical dimensions as the dysfunctional patient, determining the physiologic characteristics for the dysfunctional patient, determining indicated correction factors corresponding to any differences between the dysfunctional patient's physiologic characteristics and those of the matched template, and adjusting therapy delivery by any indicated correction factors to stimulate the patient in a pattern more closely matched to the physiologic characteristics of the matched template.

Another embodiment includes a method of adjusting an implantable therapy device for adaptation to the needs of an individual patient, the method comprising measuring a plurality of physiologic parameters of a dysfunctional patient at least partially via an implantable device, comparing the plurality of measured physiologic parameters of the dysfunctional patient with data indicative of corresponding physiologic parameters for a matched group of at least one eufunctional patient, the data being stored by the implantable device, and dynamically adjusting therapy delivery by the device such that the plurality of physiologic parameters of the dysfunctional patient are brought into closer conformance with those of the matched group of at least one eufunctional patient.

A further embodiment includes an implantable cardiac stimulation device configured for connection with one or more implantable stimulation and sensing electrodes, the device comprising an implantable stimulation generator, data storage configured to store at least one template of data indicative of normal physiologic activity, the template being matched to have data representative of persons having similar anatomic dimensions as an implantee, and a controller in communication with the implantable stimulation generator to induce generation and delivery of therapeutic stimulation and in communication with the data storage and wherein the controller is further configured to receive a plurality of signals from implanted sensing locations indicative of physiologic activity corresponding to that of the stored template and wherein the controller further compares the plurality of sensed signals to the stored template and adjusts delivery of the therapeutic stimulation such that the physiologic activity more closely conforms to the template.

An additional embodiment includes an implantable cardiac stimulation device for stimulating a heart of a patient, the device comprising a plurality of leads adapted to be implanted at a plurality of spaced apart locations adjacent the heart of the patient wherein at least some of the plurality of leads both provide therapeutic stimulation to the heart of the patient and also receive signals indicative of cardiac activity and a controller that induces delivery of therapeutic stimulation to the heart of the patient via the plurality of leads and receives the signals indicative of the functioning of the heart from the plurality of leads wherein the controller is associated with memory in which desired timing characteristics of the beating of the patient's heart are stored, wherein the stored desired timing characteristics comprise characteristics selected from at least one representative person having desired heart contraction characteristics corresponding to the patient and wherein the controller at least periodically induces the plurality of leads to sense cardiac signals corresponding to the desired timing characteristics and compares the sensed signals to the desired timing characteristics. These and other objects and advantages of the invention will become more

BRIEF DESCRIPTION OF THE DRAWINGS

FIG. 3A illustrates an exemplary waveform of a surface ECG.

FIG. 3B illustrates an exemplary waveform of impedance over time between electrodes arranged adjacent a patient's right ventricle and superior vena cava respectively.

FIG. 3C illustrates an exemplary waveform of an IEGM sensed between an RV tip and RV coil electrodes.

FIG. 3D illustrates an exemplary waveform of an IEGM sensed between an RV tip and LV tip electrodes.

FIG. 3E illustrates an exemplary waveform of impedance over time between an RV tip and RV coil electrodes.

FIG. 3F illustrates an exemplary waveform of impedance over time between an RV tip and LV electrodes.

DETAILED DESCRIPTION

Reference will now be made to the drawings wherein like numerals refer to like parts throughout. The following description includes the best mode presently contemplated for practicing the invention. This description is not to be taken in a limiting sense but is made merely for the purpose of describing the general principles of the invention. The scope of the invention should be ascertained with reference to the issued claims.

Figure 1:
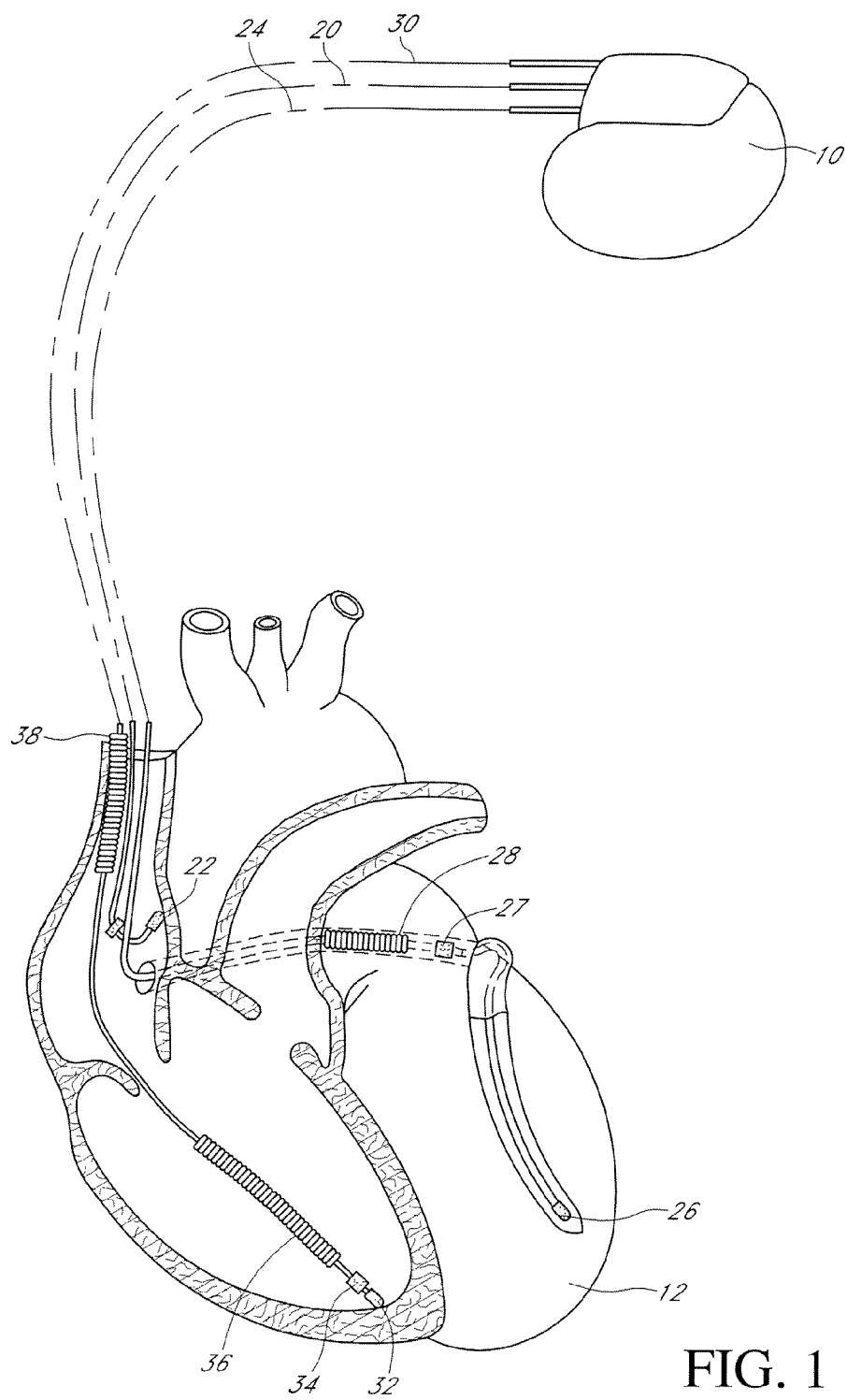
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
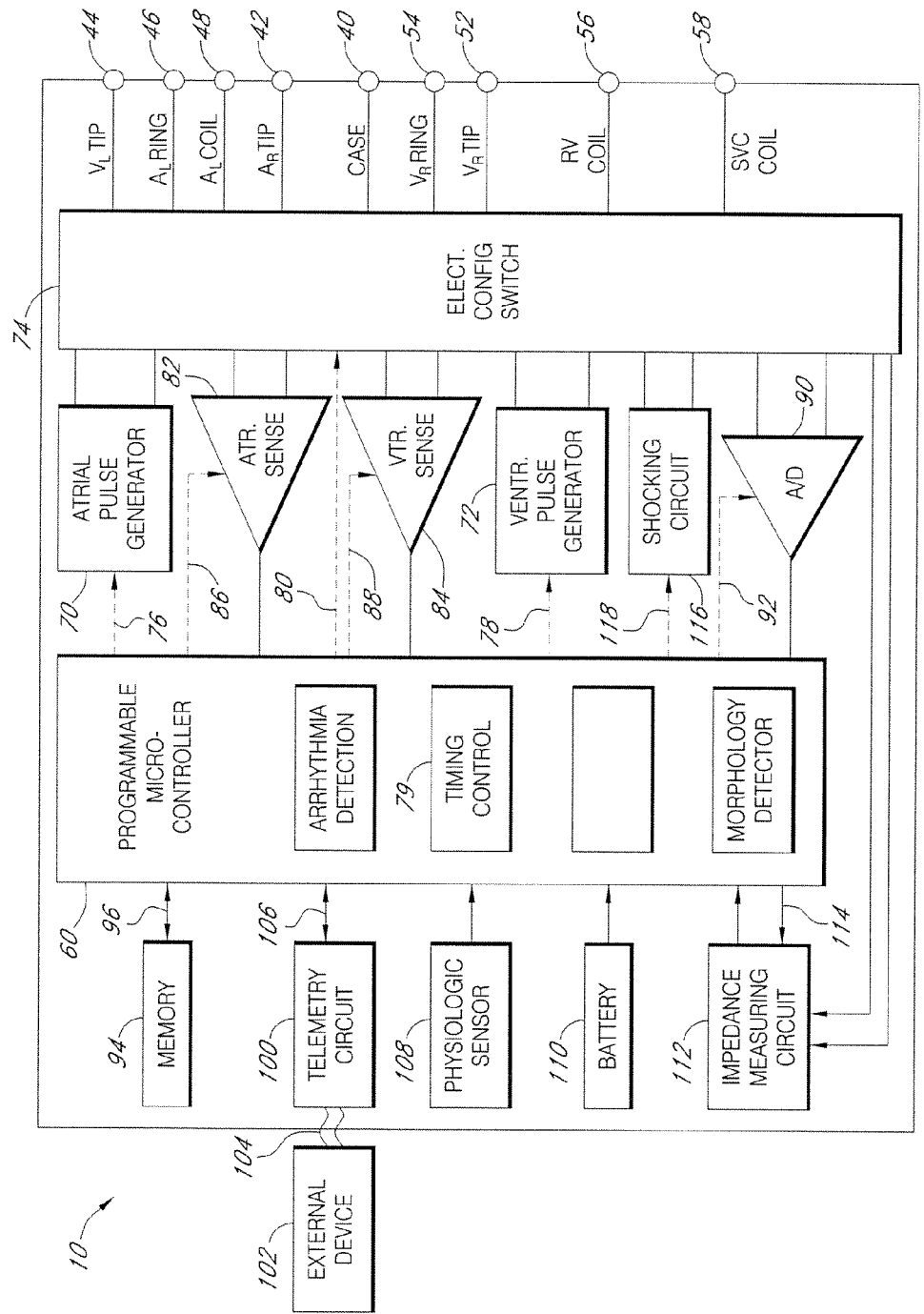
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIGS. 3A-3F illustrate various waveforms of different physiologic parameters determined over multiple cycles of cardiac activity for an eucontractile patient. As used herein, eucontractile refers to a patient exhibiting electro-mechanical parameters of their cyclical cardiac depolarization/repolarization which is substantially normal and healthy. Eucontractile does not necessarily imply that the patient is in all respects healthy and normal, but simply that the time varying electro-mechanical parameters are substantially similar to those of an otherwise comparable healthy person.

In certain embodiments, the waveforms illustrated in FIGS. 3A-3F correspond to a composite or normalized curves corresponding to a representative patient population. For example, in one embodiment, the anatomical dimension characteristics of patients are screened and grouped into similar sets. Thus, in one embodiment, the waveforms illustrated in FIGS. 3A-3F correspond to those of patients having similar anatomical dimensions, for example, dimensions relating to their heart. In one embodiment, radiographic and/or 3-dimensional echocardiographic assessment of patient's heart chamber geometries and dimensions are measured over a plurality of eucontractile patients. This larger population is then grouped into subpopulations to establish separate templates for at least one of the subpopulations.

In one embodiment, the cardiac geometry and dimension measurements are utilized to subcategorize the eucontractile patient data into the categories of normal cardiac size, mild biventricular dilation, moderate biventricular dilation, severe biventricular dilation, mild left ventricular dilation, moderate left ventricular dilation, and severe left ventricular dilation. Further characterizing data can be gathered in certain embodiments by measuring and determining a ratio of the cardiac silhouette to a lateral thoracic diameter as measured by plane radiographs. Measurement and characterization of a patient's cardiac geometry/dimension is valuable, particularly with patients having enlarged hearts, as timing of depolarization/repolarization events would be expected to be more delayed between electrodes that are positioned a further distance apart, for example, further than in patients having smaller/more normally sized hearts.

As previously noted, the eucontractile data is gathered from patients exhibiting normal electro-mechanical characteristics of their cardiac activity. In certain embodiments, this would include patients having a history of cardiac arrest without ischemic heart disease or cardiomyopathy, e.g., Brugada or Long QT syndrome patients. Such patients can be provided with implantable devices which measure intracardiac electrograms (IEGMs) and internally sensed impedance measurements. In other embodiments, additional data can be acquired during electrophysiology studies and/or via surface ECGs, without necessarily using implantable leads.

In certain embodiments, the eucontractile data is gathered, at least partially, via electrophysiology studies (EPS), such as performed in an electrophysiology (EP) lab. Mapping of a subject's cardiac conductive pathways can be performed. Data gathered can include determinations of automaticity, myocardial excitability, refractoriness, and regional and global conductivity. Data can be gathered over a range of subject metabolic rates, such as during exercise and rest and/or under Dobutamine to develop rate related data.

Figure 3:
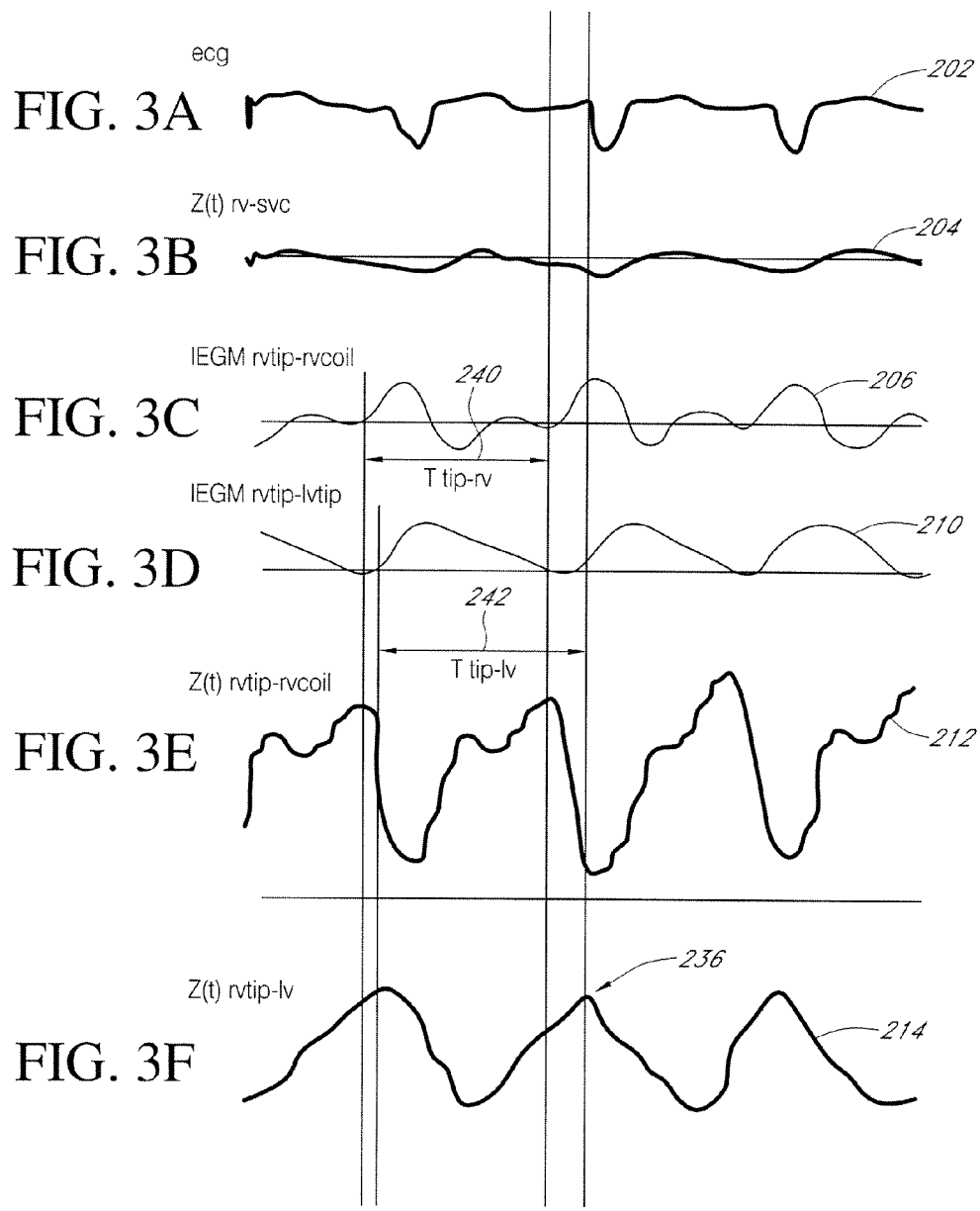
FIGS. 3A-3F illustrate various waveforms indicative of different physiologic parameters determined for multiple cycles of cardiac activity for an eucontractile patient.

FIG. 3A illustrates an exemplary waveform corresponding to a surface ECG 202. The surface ECG 202 is a well known and understood diagnostic tool based on measurements taken with multiple electrodes placed at determined locations on the patient's skin surface and representative of the underlying cardiac activity. FIG. 3B illustrates an exemplary waveform of electrical impedance over time between electrodes arranged adjacent a patient's right ventricle and superior vena cava (SVC), respectively.

FIG. 3C illustrates an IEGM waveform 206 as measured between an RV tip electrode and an RV coil electrode. Similarly, FIG. 3E illustrates a time varying impedance curve 212 as measured between an RV tip and an RV coil electrode.

FIG. 3D illustrates an exemplary waveform of an IEGM sensed between an RV tip and an LV tip electrode. Similarly, FIG. 3F illustrates a time varying impedance curve 214 as measured between an RV tip and an LV electrode.

FIGS. 3C and 3D illustrate, for example, A-V delays within a single cardiac cycle as well as A-A and V-V delays across consecutive cardiac cycles as indicated by IEGM signals. FIGS. 3E and 3F illustrate corresponding delays as indicated by impedance measurements. As previously noted, the device 10 is capable of varying these as well as other delays. Various embodiments provide the ability to optimize these as well as other operational parameters of the device 10, for example in a rate responsive manner.

As previously noted, the eucontractile data illustrated in FIGS. 3A-3F is in certain embodiments based upon measurements made of a plurality of patients having similar cardiac geometries/dimensions. Thus, the activity illustrated by one or more of FIGS. 3A-3F may not correspond precisely to any given individual patient, but is rather illustrative generally of normal eucontractile characteristic. FIGS. 3A-3F illustrate certain monuments or characteristic features of interest in characterizing eucontractile activity.

In one embodiment, FIG. 3C illustrates an onset of the IEGM RV tip to RV coil 206 as that upward going zero crossing point of the curve 206 indicating the onset of the activity. FIG. 3E illustrates a peak of the impedance Z(t) RV tip to RV coil 232. The peak 232 corresponds to the peak amplitude of transmyocardial impedance during the time of maximal systolic wall thickness. The timing difference between the occurrence of the onset of IEGM RV tip to RV coil 230 to the associated peak of impedance Z(t) RV tip to RV coil 232 defines an electro-mechanical coupling interval T tip to RV 240. The coupling interval T tip to RV 240 indicates the lag or delay between the onset of electro-chemical activity indicated by the IEGM RV tip to RV coil 206 and the subsequent peak myocardial activity indicated by the impedance Z(t) RV tip to RV coil 212 for a representative eucontractile patient.

Similarly, FIG. 3D illustrates an onset of IEGM RV tip to LV tip 234 corresponding to the onset of electrochemical activity. This is followed by a subsequent peak of impedance Z(t) RV tip to LV tip 236. The timing difference between the onset 234 and impedance peak 236 defines an electro mechanical coupling interval T tip to LV 242. It will be noted that in this embodiment the coupling interval T tip to LV 242 is longer than the coupling interval T tip to RV 240. This would be expected as the coupling interval T tip to LV 242 corresponds to both an increase in physical distance between the measurement points as well as presence of more conduction delay along this vector. It is also illustrative to compare the peak-to-peak differences in the impedance curves 204, 212, and 214. The peak-to-peak or amplitude difference is the least for the impedance Z(t) RV to SVC 204 as this vector traverses the least myocardium. The impedance differences are greatest between the RV tip and LV electrodes as this vector incorporates both right ventricular and left ventricular myocardium as well as the intraventricular septum.

Figure 4:
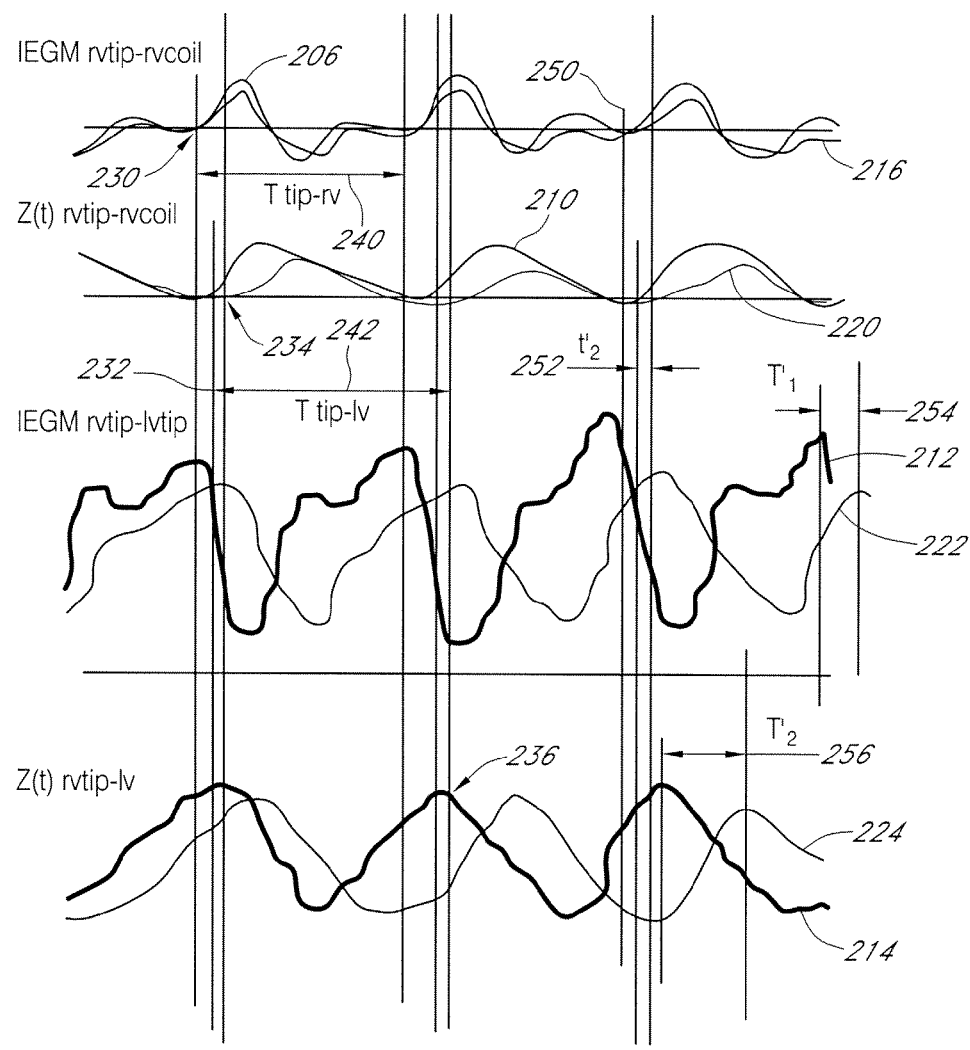
FIG. 4 illustrates an overlay of exemplary waveforms of a representative eucontractile patient and a dysfunctional patient with one embodiment of determining correction factors.

FIG. 4 illustrates one embodiment of overlaid waveforms indicative of electro-mechanical cardiac activity for eucontractile patients and patients having myocardial impairment with the eucontractile and impaired patients having similar cardiac anatomical geometries and dimensions. FIG. 4 includes the waveforms 206, 210, 212, and 214 as previously shown and described for FIGS. 3C-3F. FIG. 4 also illustrate a waveform from a dysfunctional patient corresponding to an IEGM RV tip to RV coil 216. The dysfunctional IEGM 216 is overlaid with the eucontractile IEGM 206. Similarly, a dysfunctional patient's IEGM RV tip to LV tip 220 is illustrated overlaid with a corresponding eucontractile patient's IEGM RV tip LV tip 210.

FIG. 4 also illustrates waveforms corresponding to mechanical activity in this embodiment including the eucontractile impedance curves 212 corresponding to impedance Z(t) RV tip to RV coil and 214 corresponding to impedance Z(t) RV tip LV. These eucontractile waveforms are overlaid with dysfunctional patient's waveforms indicative of their mechanical cardiac activity characteristics. This is illustrated in this embodiment with overlaid waveforms impedance Z(t) RV tip to RV coil 222 for the dysfunctional patient and the impedance curve Z(t) RV tip to LV 224 for the dysfunctional patient. FIG. 4 also illustrates the eucontractile electro-mechanical coupling intervals T tip to RV 240 and T tip to LV 242.

FIG. 4 also illustrates that this embodiment also includes the calculation of temporal correction factors. In this embodiment, an examination or evaluation is made between the dysfunctional patient's electro-mechanical cardiac activity as compared to an otherwise comparable eucontractile patient's. In one embodiment, the electrical characteristics of the dysfunctional patient are compared to those of a corresponding eucontractile patient for possible indications of a stimulation deficit.

A first temporal correction factor $t'_1$ would indicate a stimulation deficit and be exhibited by a temporal mismatch between the curves 206 and 216. In this embodiment, while the dysfunctional and the eucontractile patients exhibit magnitude differences in the respective IEGM RV tip to RV coil waveforms 206, 216, the waveforms are substantially temporally synchronized and in this embodiment a first temporal correction factor $t'_1$ is effectively null. Thus, in this embodiment, this particular dysfunctional patient is not exhibiting a stimulation deficit in the RV tip to RV coil dimension and modification of their therapy in this aspect would not be indicated.

In this embodiment, the patient does exhibit a degree of stimulation deficit along the IEGM RV tip to LV tip dimension. More particularly, it can be seen that a difference exists in the temporal dimension between the IEGM curves 210, 220 for the eucontractile and dysfunctional patients, respectively. Thus, in this embodiment, a second temporal correction factor $t'_2$ 252 would be indicated. The second temporal correction $t'_2$ 252 indicates a time by which therapeutic stimulation should be pre-excited in its delivery to the patient to compensate for the temporal mismatch in the dysfunctional patient's electrical cardiac activity along the RV tip to LV tip dimension.

Similarly, temporal correction factors can be evaluated for the patient's mechanical activity for indication of contraction deficits. In this embodiment, a third temporal correction factor $T'_1$ would be indicated for the patient as indicated by the reference designator 254 of FIG. 4. The third temporal correction factor $T'_1$ corresponds to a delay or mismatch in the dysfunctional patient's impedance measurement z(t) along the RV tip to RV coil dimension. A fourth temporal correction factor $T'_2$ 256 would also be indicated in this embodiment due to the delay or mismatch of the dysfunctional patient's impedance curve z(t) RV tip to LV 224 as compared to the eucontractile impedance curve z(t) RV tip to LV 214. The third and fourth temporal correction factors $T'_1$ and $T'_2$ 254, 256 correspond to contraction deficits in the dysfunctional patient along the RV tip to RV coil and RV tip to LV vectors, respectively.

In this embodiment, any indicated temporal correction factors, for example, for stimulation deficits and/or contraction deficits along a given dimension or vector are summed to obtain a total electro-mechanical temporal correction factor indicated for delivery of therapy along that vector. For example, in one embodiment, the first temporal correction factor $t'_1$ is effectively null corresponding to the lack of contraction deficits in this patient along this vector and the total temporal correction factor would correspond to the third temporal correction factor corresponding to the dysfunctional patient's contraction deficit along the RV tip to RV coil dimension. Similarly, the total electro-mechanical temporal correction factor needed along the RV tip to LV dimension would equal $t'_2$ plus $T'_2$ to account for both the stimulation deficit and contraction deficit along the RV tip to RV vector. The total electro-mechanical temporal correction factors are used to adjust the delivery of therapeutic stimulation to attempt to restore the dysfunctional patient's cardiac activity to closer conformance with the electro-mechanical cardiac activity of a comparable eucontractile patient.

Again, in certain embodiments, any indicated temporal correction factors are used to determine a pre-excitation period or delay to adjust the timing of delivery of therapeutic stimulations. In certain embodiments, the temporal correction factors are determined over a range of metabolic rates. It will be understood that in certain applications the indicated temporal correction factors will vary as a function of rate. In certain implementations, a given correction factor can be null for some rates and present at other rates.

Determination of appropriate stimulation strength, for example voltage and current to be delivered can also be determined through analysis of evoked potentials as currently employed in known pacing systems. Alternatively, or in addition, determination of appropriate therapeutic stimulation intensity is based in certain embodiments on measurements of threshold data obtained during evaluation of device function, for example, via capture threshold measurements.

Figure 5:
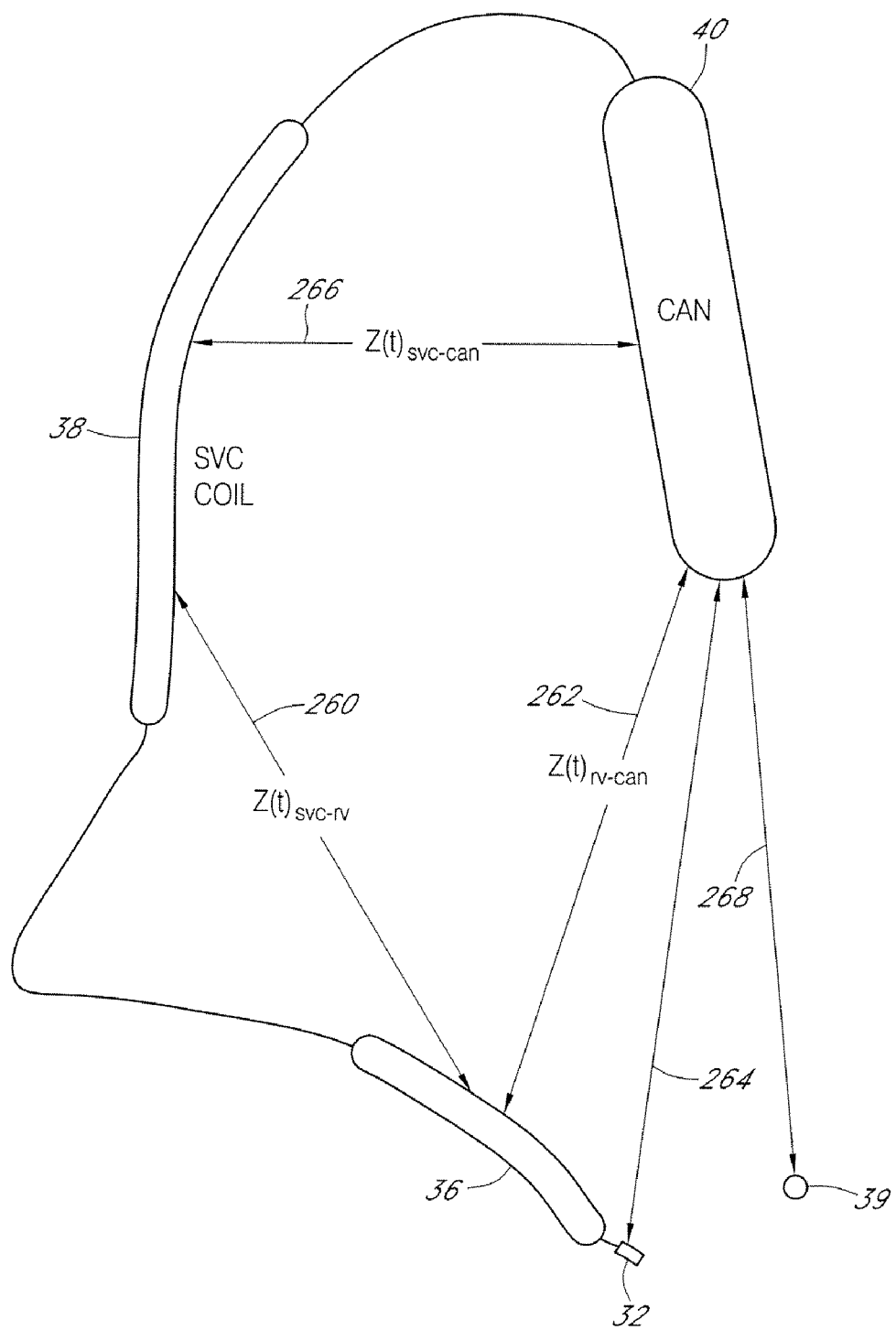
FIG. 5 is a schematic illustration of one embodiment of multi-dimensional determination of electro-mechanical activity vectors.

FIG. 5 is a schematic illustration of one embodiment of multi-dimensional determination of electro-mechanical activity vectors. As illustrated in FIG. 5, in this embodiment, a plurality of electrodes are configured for arrangement at a variety of implanted locations. These electrodes include in this embodiment an RV tip electrode 32, an RV coil electrode 36, an SVC coil 38, an LV electrode 39, and a can or housing electrode 40. It will be understood that these multiple electrodes are configured to be arranged so as to be displaced along multiple spatial dimensions. For example, the electrodes 32, 36, 38, 39, and 40 are configured to be displaced from each other along a patient's left to right dimension, along a front to back or anterior posterior dimension, as well as along a top to bottom or cephalo-caudal dimension. In this embodiment, the plurality of electrodes define multiple spatial temporal vectors therebetween. In this embodiment, these vectors include a first spatial temporal vector 260 extending between the SVC coil 38 and RV coil 36. This embodiment also defines a second spatial temporal vector 262 extending between the RV coil 36 and the can 40. A third spatial temporal vector 264 extends between the RV tip electrode 32 and the can 40. A fourth spatial temporal vector 266 extends between the SV coil 38 and the can 40. A fifth spatial temporal vector 268 extends between the LV electrode 39 and the can 40.

Each of these vectors define time varying impedance characteristics which can be evaluated for indications of the patient's condition. The time varying impedance characteristics, for example, including IEGM and impedance measurements taken along these multiple vectors, can be utilized to determine one or more temporal correction factors to adjust delivery of therapy to restore the dysfunctional patient's cardiac activity into closer electro-mechanical conformance with a corresponding eucontractile patient.

Figure 6:
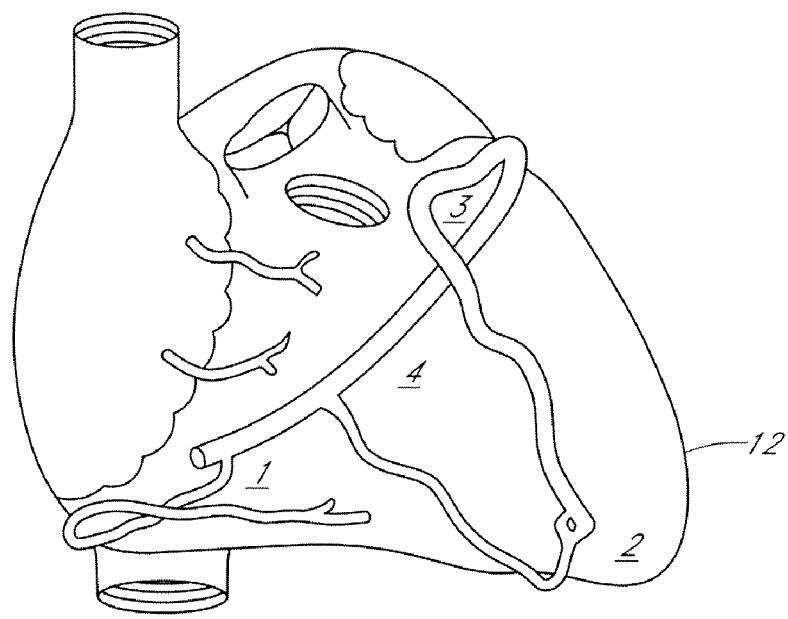
FIG. 6 is a schematic illustration of a generally helical spatial temporal arrangement of stimulation delivery sites about a patient's heart.

FIG. 6 illustrates another embodiment of adjustment of the spatial temporal delivery of synchronized cardiac therapy. As previously noted, eucontractile activity can be characterized by a progressively generally helically extending coiling and uncoiling motion as the depolarization/repolarization progresses throughout the patient's heart 12. In certain implementations, it would be preferred that therapeutic stimulations be provided in the following spatial temporal path and include atrial depolarization and the appropriately time atrial-ventricular delay time. An initial stimulation would occur in the right atrium and conduct to the left heart beginning with the left atrium extending toward the AV groove where the coronary sinus plane often lies. The stimulation would ideally be provided adjacent to the coronary sinus OS, a region where multipolar pacing systems can contain electrodes. This would be followed by delivery of stimulation of the interventricular septum and then adjacent to the right ventricular apex. This would then be followed by stimulation adjacent the most lateral coronary sinus followed by the most posterior coronary sinus location. Delivery of stimulation along this spatial temporal path would closely replicate the eucontractile helical pattern desired.

Figure 7:
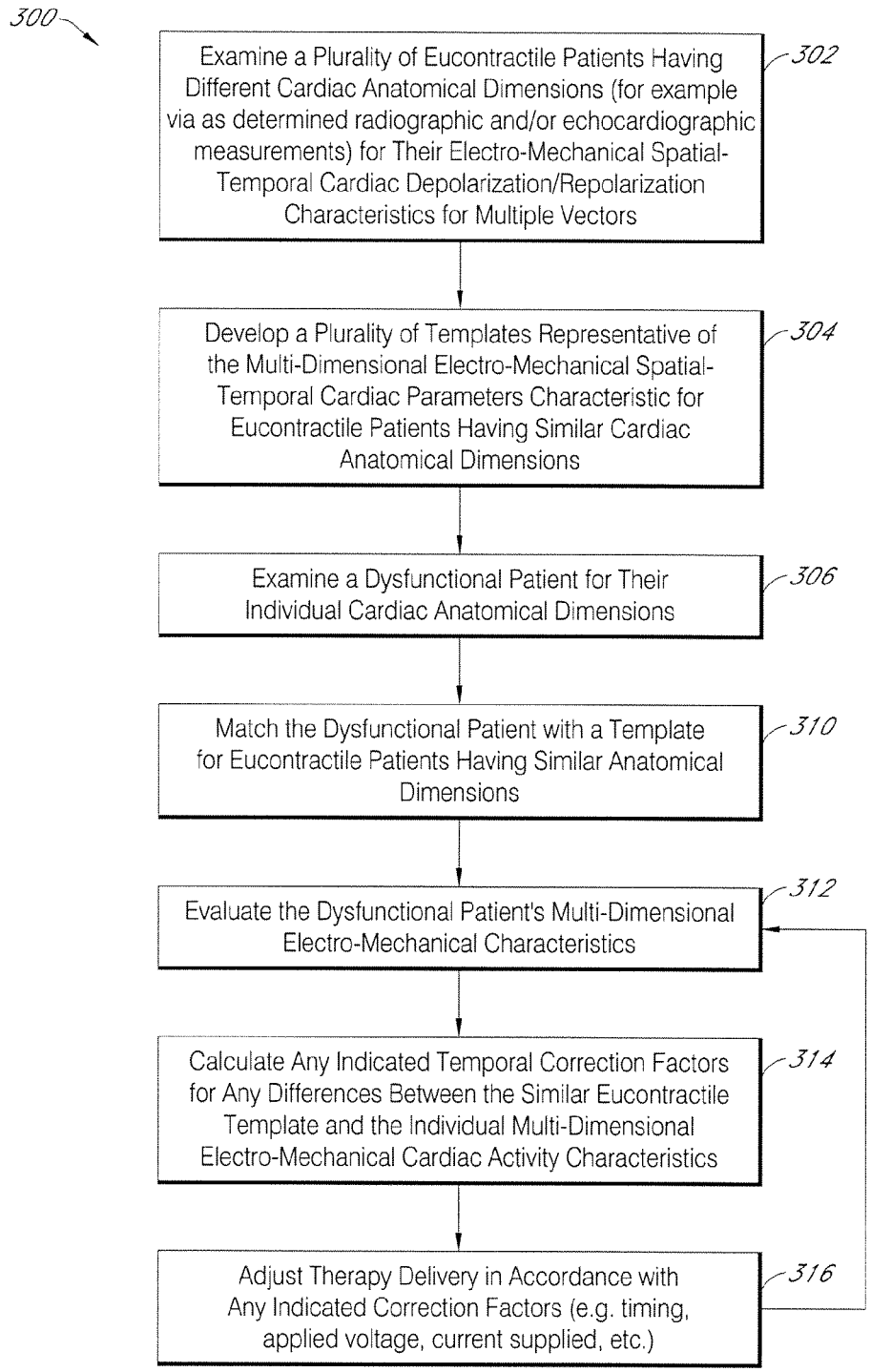
FIG. 7 is a flow chart of one embodiment of a system and method of individually adapting cardiac electro-mechanical synchronization therapy.

FIG. 7 illustrates a flow chart of one embodiment of a method of optimizing or individually adapting cardiac electro-mechanical synchronization therapy. In this embodiment, the method 300 begins in a block 302 wherein a plurality of eucontractile patients are examined. The plurality of eucontractile patients would preferably include a number of different patients having a range of cardiac anatomical dimensions. The eucontractile patients' anatomical dimensions can be determined, for example, via radiographic examinations and/or echocardiographic measurements. The measurement and evaluation of the patient's cardiac anatomical dimensions can include determination of net volume ratios, overall cardiac volume, bi-ventricular or left ventricular dilation, etc.

The examination of block 302 also includes in this embodiment evaluation of the plurality of eucontractile patients to determine the spatial temporal cardiac depolarization/repolarization characteristics along multiple spatial vectors. As the method 300 is ultimately intended at least in part for application to dysfunctional patients who are provided with an implantable cardiac therapy device, it is preferred in certain implementations that the examination of block 302 include measurements from implanted sites, e.g., to include IEGMs. Generally, the examination of block 302 is directed to a plurality of eucontractile patients to determine representative characteristics of the electrical parameters of their cardiac activity as well as mechanical parameters of the cardiac activity and to develop these representative parameters across a variety of patient population having a range of cardiac anatomical dimensions.

Following from block 302 is a block 304 wherein a plurality of templates are developed. As used herein, template refers to a representative characterization of an eucontractile patient and includes their approximate cardiac anatomical dimensions and a spatial temporal characterization of their electro-mechanical cardiac activity. The given template would provide an approximation for the normal healthy or eucontractile electro-mechanical characteristics of a patient having similar cardiac dimensions/geometries.

The method 300 also includes in this embodiment a block 306 wherein a dysfunctional patient, for example a patient suffering from myocardial disease, is examined to determine their individual cardiac anatomical dimensions. The examination of block 306 would proceed in a similar manner to the examination of block 302, for example, including radiographic examination and/or echocardiographic measurements. It would be understood that the block 306 can precede, follow, or occur in parallel with one or both of the blocks 302 and 304.

In a block 310, the examination results from block 306 are used to match the dysfunctional patient with an appropriate template. The matching of state 310 identifies a template developed for eucontractile patients having similar cardiac dimensions as the dysfunctional patient's. It will be understood that the match of block 310 will in many implementations be an approximation such as the eucontractile patient has similar but not exactly the same anatomical dimensions as for a matched template. The closeness of the match of block 310 will depend on the number of patients examined in the block 302 as well as the available time and monetary resources available to develop the templates. An appropriate degree of similarity or match to be made in block 310 will be readily understood by one of ordinary skill.

The method 300 also includes a block 312 wherein the dysfunctional patient's electro-mechanical cardiac activity is characterized in multiple spatial and temporal dimensions. In one embodiment, the evaluation of block 312 would include the development of one or more of the waveforms 216, 220, 222, and/or 224 as previously illustrated and described with respect to FIG. 4. In this embodiment, the method 300 also includes block 314 wherein any indicated temporal correction factors are calculated. Indicated temporal correction factors correspond to any differences between the similar eucontractile template and the individual patient's multi-dimensional electro-mechanical cardiac activity characteristics.

Then in a block 316, therapy delivery is adjusted in accordance with any indicated temporal correction factors determined from block 314. The adjustment of block 316 can also include adjustment of stimulation magnitude parameters, such as applied voltage and/or current delivered. The adjustment of block 316 is performed to optimize or individually adjust generation and delivery of therapy. The method 300 strives to achieve closer conformance to eucontractile cardiac activity for the patient suffering dysfunction. This provides optimized or individually adapted CRT for the individual requirements and characteristics of a given patient. While it is not expected that application of the method 300 will result in fully eucontractile activity for all HF patients, the method 300 will provide more accurately individualized therapy expanding the patient population who can benefit from this individually adapted CRT as well as optimizing CRT for those patients already known to benefit.

As CRT frequently strives to actively alter bi-ventricular synchronization in a treated patient, in certain embodiments, the method 300 proceeds at least partially in an iterative manner. In one particular embodiment, following the adjustment of block 316, the method proceeds with subsequent iterations of blocks 312, 314 and 316. It will be understood that in certain implementations a delay may be introduced between subsequent iterations to allow an accommodation period for the revised therapy. It will be further appreciated that in certain implementations, the adjustment of block 316 can result in forced fusion. In certain cases, in order to most closely approximate the impedance and IEGM waveforms of an eucontractile patient, therapeutic stimulation delivered to the dysfunctional patient, for example RV or LV stimulation, may indicate that the stimulation be applied so as to create fusion in one or more chambers. For these patients' cases, one or more chambers may experience partial intrinsic and later partial paced conduction. For example, such operation may be optimal in patients that have only a small regional conduction impairment.

The method 300 can also be readily applied to multiple and new lead configurations. For example, the multi-dimensional spatial temporal analysis and adjustment provided by the method 300 can be readily applied to any of a variety of number and relative spatial positioning of sensing and/or stimulation electrodes. Certain implementations are simplified when electrodes provide both sensing and stimulation functionality, however, this is certainly not a requirement and the method 300 can be readily applied to systems employing separate sensing and/or stimulation electrodes. It will also be understood that therapy provided by the method 300 can be provided in combination with other therapy, such as medication regimens and/or ablation therapy. It will be further understood that an iteration of the method 300 can be triggered asynchronously, such as via a command signal provided by an external device 102 in telemetric communication with the implantable device 10 to refine therapy provided by the method, for example, following an ablation procedure and/or a change in the patient's medication.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A method of determining therapy for an individual patient, the method comprising:

determining representative normal physiologic characteristics for a plurality of patients having a range of anatomical dimensions;

developing a plurality of normal templates wherein each template indicates the representative normal physiologic characteristics of a group of patients having similar anatomical dimensions;

measuring the anatomical dimensions of a dysfunctional patient;

matching the dysfunctional patient with a template for patients having similar anatomical dimensions as the dysfunctional patient;

determining the physiologic characteristics for the dysfunctional patient;

determining indicated correction factors corresponding to any differences between the dysfunctional patient's physiologic characteristics and those of the matched template; and adjusting therapy delivery by any indicated correction factors to stimulate the patient in a pattern more closely matched to the physiologic characteristics of the matched template;

wherein the dysfunction comprises cardiomyopathy and the therapy comprises cardiac resynchronization therapy.

* * * * *